United States Patent [19]

Shanton

[11] Patent Number: 5,206,380

[45] Date of Patent: Apr. 27, 1993

[54] DIVINYL CARBINOL OR CARBINOL DERIVATIVE CHROMOGENIC COMPOUNDS

[75] Inventor: Kenneth J. Shanton, Neenah, Wis.

[73] Assignee: The Wiggins Teape Group Limited, Basingstoke, England

[21] Appl. No.: 894,814

[22] Filed: Jun. 8, 1992

Related U.S. Application Data

[62] Division of Ser. No. 613,019, Nov. 15, 1990, Pat. No. 5,143,891.

[30] Foreign Application Priority Data

Nov. 15, 1989 [GB] United Kingdom ............... 8925802

[51] Int. Cl.⁵ .................................... C07D 209/82
[52] U.S. Cl. ...................... 548/444; 548/455; 548/509; 564/384; 564/434; 564/443
[58] Field of Search ............ 564/434, 443, 384; 548/444, 455, 509

[56] References Cited

U.S. PATENT DOCUMENTS

| | | | |
|---|---|---|---|
| 3,257,202 | 6/1966 | Schlesinger et al. | 96/1.5 |
| 3,957,288 | 5/1976 | Lemahieu et al. | 282/27.5 |
| 4,987,262 | 1/1991 | Kazuyuki et al. | 564/443 |

FOREIGN PATENT DOCUMENTS

| | | |
|---|---|---|
| 0315901 | 5/1989 | European Pat. Off. |
| 2212788 | 7/1974 | France |
| 512477 | 9/1939 | United Kingdom |
| 1342971 | 1/1974 | United Kingdom |
| 1456208 | 11/1976 | United Kingdom |

OTHER PUBLICATIONS

Zimmerman et al., "Cyclopropanols and the Di-π-methane Rearrangement: Mechanistic and Exploratory Organic Photochemistry", 55 *J. Organic Chemistry* No. 16, 3792-03 (1988).

*Primary Examiner*—Richard L. Raymond
*Attorney, Agent, or Firm*—Burns, Doane, Swecker & Mathis

[57] ABSTRACT

A chromogenic compound for use in pressure- or heat-sensitive record material has the general formula (I):

$$R_1-CH=CH-CR_3(OR_4)-CH=CH-R_2 \quad (I)$$

in which:

$R_1$ and $R_2$ are the same or different and each is a group of one of the formulae (II):

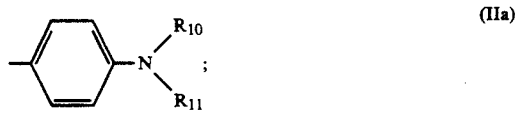

(IIa)

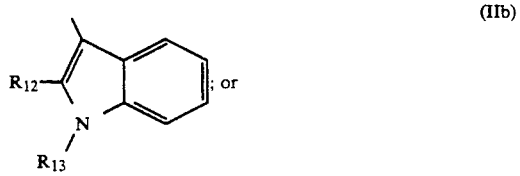

(IIb)

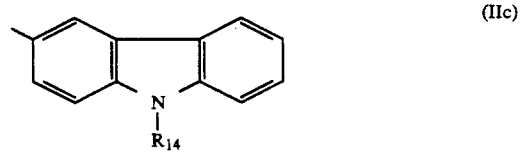

(IIc)

in which the benzene ring of the group of formula (IIa) is optionally further substituted, and in which:

$R_{10}$ and $R_{11}$ are each independently hydrogen or an optionally-substituted alkyl, aryl or aralkyl group, or $R_{10}$ and $R_{11}$ together with the nitrogen atom to which they are attached form an optionally-substituted heterocyclic ring, which may include one or more further hetero atoms;

$R_{12}$, $R_{13}$ and $R_{14}$ are each independently hydrogen or an optionally-substituted alkyl, aryl or aralkyl group;

$R_3$ is an optionally-substituted aryl group; and $R_4$ is hydrogen or an optionally-substituted alkyl, aryl or aralkyl group.

9 Claims, No Drawings

DIVINYL CARBINOL OR CARBINOL DERIVATIVE CHROMOGENIC COMPOUNDS

This application is a divisional of application Ser. No. 07/613,109, filed Nov. 15, 1990, now U.S. Pat. No. 5,143,891.

This invention relates to chromogenic compounds and their use in record material, particularly pressure-sensitive and heat-sensitive record material. In such record material, image formation occurs by a reaction between the chromogenic material and a suitable colour developer to produce a coloured species.

As is well known in the art, pressure sensitive record material typically functions by separating the colour reactive components by a pressure rupturable barrier. Most commonly this barrier is provided by microencapsulating a solution in a suitable organic solvent of one of the reactive components. On application of imaging pressure the microcapsules are ruptured, liberating the solution of one of the reactive components into reactive contact with the other component thereby forming a coloured mark or image corresponding to the applied imaging pressure. It is also known to use other forms of pressure rupturable barrier such as a dispersion of a solution in a waxy continuous layer or a honeycomb structure instead of microcapsules.

Such pressure sensitive record material can be of two basic types: the so-called "transfer" and "self-contained" types. In the transfer type the reactive components are present in coatings on facing surfaces of upper and lower sheets, the coating on the lower surface of the upper sheet comprising the isolated and usually microencapsulated solution of one reactive component and the coating on the upper surface of the lower sheet comprising the other component. Most commonly it is the chromogenic material which is present in the microcapsules in the coating on the lower surface of the upper sheet and the colour developer which is present in the coating on the upper surface of the lower sheet. This is the so-called "normal transfer" pressure sensitive sytem. An alternative to this is the so-called "reverse transfer" system in which colour developer is dissolved and microencapsulated and the chromogenic material is present, usually adsorbed on a suitable particulate carrier, in the coating on the upper surface of the lower sheet.

The sheets carrying microencapsulated material on their lower surfaces are usually referred to as "CB" (coated back) sheets and the sheets carrying a reactive coating on their upper surfaces are usually referred to as "CF" (coated front) sheets. In addition it is common to use intermediate sheets which carry appropriate coatings on both upper and lower surfaces and these are usually referred to as "CFB" (coated front and back) sheets.

In self-contained pressure sensitive sheet record material, both reactive components are present on or in a single sheet. Premature reaction is inhibited by microencapsulating one of the components, usually the electron donating chromogenic material. The reactive components can be present in one or more coatings on a surface of the sheet (coated self-contained) or dispersed within the body of the sheet (loaded self-contained).

In heat-sensitive sheet record material, the reactive components, i.e. the chromogenic material and the colour developer, are initially present in a mutually unreactive state and are then enabled to react together by changes brought about by heat. Most commonly this is achieved by including the chromogenic material and colour developer in the heat-sensitive record material as solids. On heating the record material, the chromogenic material and/or the colour developer and/or another component of system melts and thus permits reactive contact between the chromogenic material and the colour developer. As an alternative to the arrangement just described, the chromogenic material and the colour developer may be microencapsulated in solution in a similar manner as for pressure sensitive record materia. Imaging then occurs on heat-induced rupture or increased wall permeability of the capsules.

Numerous chromogenic compounds have been used or proposed for use in record material as described above. Examples of commercially successful chromogenic compounds include phthalides such as 3,3-bis(4-dimethylaminophenyl)-6-dimethylaminophthalide (usually referred to as crystal violet lactone or CVL); indolyl phthalides such as 3,3-bis(1-N-ethyl-2-methylindol-3-yl)phthalide; fluorans, particularly amino-substituted fluorans such as 3-(N-methyl-N-cyclohexylamino)-6-chloro-7-methylfluoran and 3-diethlamino-6-methyl-7-N-phenylaminofluoran; and spirodipyrans such as 3'-i-propyl-7-dibenzylamino-2,2'-spirodi-[2H-1-benzopyran].

A number of suggestions have been made to use the carbinol bases of dyestuffs or derivatives of such carbinols, as chromogenic ccmpounds in pressure sensitive record material. Such carbinols do form colour, but do so too readily to be useful in practical systems. Typically, the carbinols will colour up during micro-encapsulation or they are so reactive that small quantities of extracapsular chromogenic material—inevitable because encapsulation is not perfectly efficient and some capsules will be inadvertently broken during handling—produce intense colouration on reaction with the base paper usually used as the substrate. So far as we are aware, no carbinol base chromogenic compound has been used commercially on a large scale because of these serious drawbacks.

An area of development of chromogenic materials in recent years has been that of compounds which have coloured forms having substantial absorption in the near infra red region of the electromagnetic spectrum. Such compounds are useful in record material (heat or pressure-sensitive) where it is desired that the image is machine readable and is therefore suitable for use in optical character recognition (OCR) applications.

We have now identified a novel class of carbinol or carbinol derivative chromogenic compounds which avoids or mitigates the above-described drawbacks of previously proposed carbinol or carbinol derivative chromogenic compounds and which gives rise to substantial infra-red absorption.

Accordingly, the present invention provides chromogenic compounds of the general formula (I):

$$R_1\text{---}CH\text{=}CH\text{---}CR_3(OR_4)\text{---}CH\text{=}CH\text{---}R_2 \qquad (I)$$

in which:

$R_1$ and $R_2$ are the same or different and each is a group of one of the formulae (II):

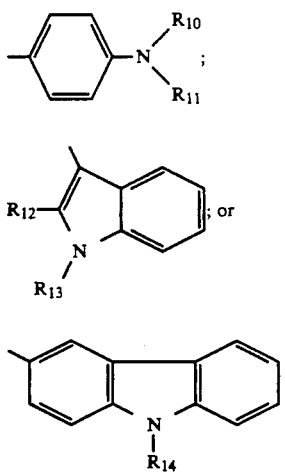

(IIa)

(IIb)

(IIc)

in which the benzene ring of the group of formula (IIa) is optionally further substituted, and in which:

$R_{10}$ and $R_{11}$ are each independently hydrogen or an optionally-substituted alkyl, aryl or aralkyl group, or $R_{10}$ and $R_{11}$ together with the nitrogen atom to which they are attached from an optionally-substituted heterocyclic ring, which may include one or more further hetero atoms;

$R_{12}$, $R_{13}$ and $R_{14}$ are each independently hydrogen or an optionally-substituted alkyl, aryl or aralkyl group;

$R_3$ is an optionally-substituted aryl group; and $R_4$ is hydrogen or an optionally-substituted alkyl, aryl or aralkyl group.

Compounds in which $R_1$ and $R_2$ are the same are generally simpler to make than those in which $R_1$ and $R_2$ are different and are therefore preferred.

In the general formula (II), alkyl groups generally have up to 12 carbon atoms, preferably up to 8 carbon atoms. The expression "alkyl group" as used in this specification includes not just straight or branched chain alkyl groups but also cycloalkyl groups, for example $C_5$ or $C_6$ cycloalkyl groups. The preferred aryl group is phenyl. The preferred aralkyl group (i.e. an aryl-substituted alkyl group) is benzyl.

When $R_{10}$ and $R_{11}$ together form part of an optionally-substituted heterocyclic ring substituent group, the ring is preferably a saturated heterocyclic ring. Examples of suitable heterocyclic ring substituents incorporating $R_{10}$ and $R_{11}$ are N-pyrrolidino, N-piperidino, N-piperazino and N-morpholino groups. The optional substitution in the case of an N-piperazino group may be an alkyl substituent, e.g. methyl, on the 4-N atom, i.e. the heterocyclic ring substituent group may be 4-N-methyl-N-piperazino.

When $R_1$ and/or $R_2$ is an optionally-substituted indole group, i.e. formula (IIb), $R_{12}$ is preferably hydrogen or a $C_1$ to $C_4$ alkyl group, e.g. a methyl group, and $R_{13}$ is preferably a $C_1$ to $C_8$ alkyl group, e.g. a methyl, ethyl or octyl group. We have so far experienced difficulty in synthesising a compound in which $R_{12}$ and $R_{13}$ are both hydrogen, and such a compound is not therefore preferred.

When $R_1$ and/or $R_2$ is an optionally-substituted carbazolyl group, i.e. formula (IIc), $R_{14}$ is preferably a $C_1$ to $C_8$ alkyl group, for example an octyl group. Compounds in which $R_1$ and $R_2$ are both carbazolyl groups have a particularly good combination of fade properties and near infra-red absorption.

Compounds of the general formulae (I) can be made from known starting materials by synthetic routes involving generally known techniques. We have successfully used the following route to make compounds of the formula (I). In the sequence outlined below the symbols $R_1$, $R_2$, $R_3$ and $R_4$ are as defined for formula (I) above.

Stage 1

This involves reaction of the appropriate aldehyde with acetone to produce an intermediate ketone

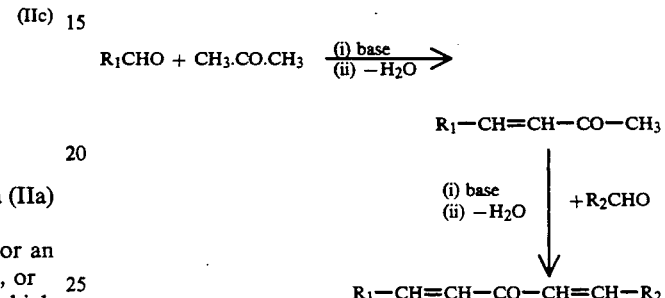

This reaction is two steps of base catalysed condensation followed by elimination of water. Where $R_1$ is the same as $R_2$ these two steps can be combined as a single step starting with 2 moles of $R_1$CHO per mole of acetone. Where $R_1$ and $R_2$ are different the first step will typically be carried out under conditions such as Claissen-Schmidt condensation conditions, e.g. using aqueous NaOH as the base. Such conditions favour 1:1 condensation and an approximately 1:1 molar ratio. The second step is then carried out using a different base e.g. methanolic NaOH.

Stage 2

This involves reaction of the intermediate ketone produced in Stage 1 with phenyl lithium, followed by addition of water to yield the carbinol compound:

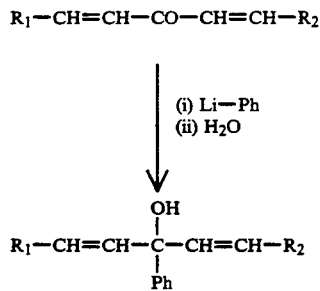

Where $R_4$ is hydrogen, the second reaction stage is particularly conveniently carried out using water to generate the carbinols of the formula (I).

We believe that the elimination of water in Stage 1 of the synthetic route described above is concerted and thus that the products produced generally have a geometry about the double bonds which is predominantly, if not exclusively, trans in relation to the groups $R_1$ to $R_2$ respectively and the group $CR_3(OR_4)$. The geometry about the double bonds is believed not to be important in terms of the major colour forming properties of the compounds and the invention therefore does not particularly distinguish between cis- and trans- isomers.

The compounds of the invention will usually be used in mark forming systems which generate blue or black perceived images. In such systems they generally will be used in combination with other chromogenic compounds such that the combination gives rise to a perceived image of the desired hue. Whatever the visual hue of the compound of the formula (I) its main importance is to contribute absorption in the near infra-red and the formulation will be adapted to take advantage of this property.

The following Examples illustrate the invention. All parts and percentages are by weight unless otherwise stated. Synthesis Examples (SE) 1 to 6 relate to the synthesis and characterization of compounds of the general formula (I). The application Example illustrates the use of the compounds of SE1 to 6 in pressure sensitive record material.

In the Synthesis Examples, at reaction Stage 2, the quantity of the lithium compound may be adjusted to get a desired balance of reaction speed, yield (completeness of reaction) and minimising of by-products.

Melting points in the Examples are open capillary uncorrected values. Yield figures are % of the theoretical maximum on the limiting intermediate precursor i.e. values are for the final step of the synthesis unless otherwise stated.

Although characterization data on the intermediate divinyl ketones is not quoted in the Synthesis Examples below, the intermediates were characterized, particularly by NMR and infra red spectroscopy. This afforded further evidence that the structures of the chromogenic compounds synthesised were of the general formula (I).

SYNTHESIS EXAMPLE 1

Bis(2-(4-dimethylaminophenyl)ethen-1-yl)phenylmethylcarbinol i.
di(2-(4-dimethylamino-2-methylphenyl)ethen-1-yl)ketone 24.45 g (0.16 mol) of 4-dimethylaminobenzaldehyde was dissolved in 150 ml industrial methylated spirit (IMS) and 5.5 ml (4.35 g; 0.075 mol) acetone to give a deep orange solution. 30 ml of 30% w/v aqueous sodium hydroxide were added to the solution, the reaction vessel was covered in aluminium foil to inhibit photochemical reactions and allowed to stand at ambient temperature for 44 hours. The resulting orange precipitate was filtered off and purified by recrystallisation from IMS to give 14.01 g (0.044 mol; 55% theory) of di(2-(4-dimethylamino-2-methylphenyl)ethen-1-yl)ketone as orange crystals. The identity of the compound was confirmed by IR and NMR spectroscopy.

ii.
bis(2-(4-dimethylaminophenyl)ethen-1-yl-phenylmethylcarbinol

This reaction was carried out in the dark and oxygen and moisture were excluded by blanketing with dry nitrogen. 3.48 g (0.011 mol) of the ketone from the previous reaction was suspended in 100 ml dry benzene in a 3 necked flask. On stirring this gave a red suspension. 8 ml of phenyl lithium solution (2M in cyclohexane; 0.01 mol) were added to give a dark green solution and the mixture was stirred at ambient temperature for 17 hours.

At the end of this period 100 ml of water were added and the mixture was agitated to ensure decomposition of excess phenyl lithium. The two layer mixture was separated and the organic (upper) layer was washed with 3×20 ml portions of water until the aqueous washings had no colour. The organic layer was dried over anhydrous sodium sulphate and the benzene removed by rotary evaporation to give an orange oil which was triturated under petroleum ether to give 2.34 g (0.0059 mol; 53.6% theory) of the title compound as a pale orange powder. This had a melting point of 158°–162° C.

EXAMPLES 2 TO 8

A series of substituted phenyl carbinol compounds of formula (I) in which $R_3$=phenyl and $R_4$=H, and in which $R_1$ and $R_2$ are the same, was made by the synthetic route described in Example 1 but substituting different starting materials for those used in Example 1. The nature of $R_1$ and $R_2$ are set out in Table 1 below, together with the melting points of the compounds and the yields obtained where the compounds were isolated. Table 1 includes the compound of Synthesis Example 1 for completeness.

In Table 1 the following abbreviations are used for substituent groups:

| Me = methyl | Et = ethyl |
|---|---|
| Oc = octyl | Ph = phenyl |
| Cz = carbazol-3-yl | In = indol-3-yl |

Substitution on groups abbreviated in this way is indicated numerically. Thus 4-Me$_2$N.Ph=4-dimethylaminophenyl and so on.

TABLE 1

| SE No | $R_1 = R_2$ | Yield % | m.p. |
|---|---|---|---|
| 1 | 4-Me$_2$N.Ph | 54 | 158–162 |
| 2 | 2-Me-4-Me$_2$N.Ph | 55 | 111–113 |
| 3 | 2-Cl-4-Me$_2$N.Ph | oily product | |
| 4 | 4-Et$_2$N.Ph | 40 | |
| 5 | 1-N-Oc-In | oily product | |
| 6 | 9-N-Et.Cz | 46 | 99–101 |

APPLICATION EXAMPLE 1

The compounds of Synthesis Examples 1, 2, 4 and 6 were separately dissolved in a mixture of partially hydrogenated terphenyls ("Santosol 340" from Monsanto) and kerosene ("Exxsol" from Exxon Chemicals) (2:1; v/v) and coated onto colour developer paper using a laboratory hand gravure coater. Two types of colour developer paper were used, having acid washed dioctahedral montmorillonite clay ('clay') and zincated phenol formaldehyde novolak resin ('resin') respectively as active ingredients. The colours developed and the values of λ max for the absorption peaks in the near infra red region of the electromagnetic spectrum are set out in Table 2 (below). All of the compounds gave strong absorption peaks in the near infra red region of the spectrum. The image developed by SE6 is noteworthy because it is especially stable to fade.

TABLE 2

| SE No | Colour Developer | | | |
|---|---|---|---|---|
| | clay | | resin | |
| | colour | λ max (nm) | colour | λ max (nm) |
| 1 | green | 838.0 | brownish-yellow | 837.0 |
| 2 | brown | 843.9 | green | 845.4 |
| 4 | red | 835 | red | 833 |
| 6 | grey | 796.4 | pale green | not measured |

I claim:

1. A chromogenic compound of the formula (I):

$$R_1-CH=CH-CR_3(OR_4)-CH=CH-R_2 \quad (I)$$

wherein $R_1$ and $R_2$ are the same or different and are selected from the group of compounds represented by the formulae (II):

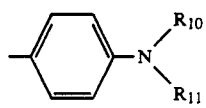 (IIa)

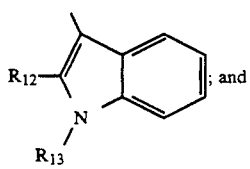 ; and (IIb)

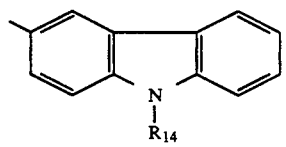 (IIc)

wherein the benzene ring of the group of formula (IIa) may be further substituted, and wherein $R_{10}$ and $R_{11}$ are each independently hydrogen or an optionally-substituted alkyl, aryl or aralkyl group, or $R_{10}$ and $R_{11}$ together with the nitrogen atom to which they are attached form an optionally-substituted heterocyclic ring, which may include one or more additional hetero atoms; $R_{12}$, $R_{13}$ and $R_{14}$ are each independently hydrogen or an optionally-substituted alkyl, aryl or aralkyl group; $R_3$ is an optionally-substituted aryl group; and $R_4$ is hydrogen or an optionally-substituted alkyl, aryl or aralkyl group.

2. A chromogenic compound as claimed in claim 1, wherein $R_1$ and $R_2$ are the same.

3. A chromogenic compound as claimed in claim 1, wherein $R_{12}$ is hydrogen, and $R_{13}$ is a $C_1$ to $C_8$ alkyl group.

4. A chromogenic compound as claimed in claim 1, wherein $R_{14}$ is a $C_1$ to $C_8$ group.

5. A chromogenic compound as claimed in claim 1, wherein $R_1$ and $R_2$ are both carbazolyl groups.

6. A chromogenic compound as claimed in claim 1, wherein $R_1$ and $R_2$, which are the same or different, are selected from the group of compounds:

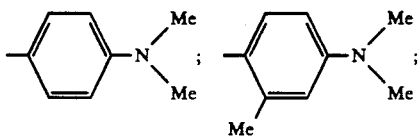

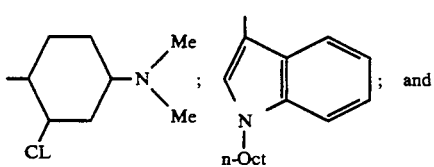

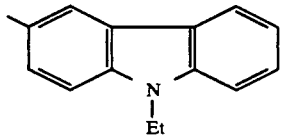

7. A chromogenic compound as claimed in claim 2, wherein $R_{12}$ is hydrogen, and $R_{13}$ is a $C_1$ to $C_8$ alkyl group.

8. A chromogenic compound as claimed in claim 2, wherein $R_{14}$ is a $C_1$ to $C_8$ alkyl group.

9. A chromogenic compound as claimed in claim 2, wherein $R_1$ and $R_2$ are both carbazolyl groups.

* * * * *